US006464852B1

(12) United States Patent
Gorfinkel et al.

(10) Patent No.: US 6,464,852 B1
(45) Date of Patent: Oct. 15, 2002

(54) MULTICAPILLARY BUNDLE FOR ELECTROPHORESIS AND DETECTION FOR DNA

(75) Inventors: Vera Gorfinkel, Stony Brook, NY (US); Mikhail Gouzman, Lake Grove, NY (US); Luryi Serge, Old Field, NY (US)

(73) Assignee: State University of New York at Stony Brook, Stony Brook, NY (US)

( * ) Notice: Subject to any disclaimer, the term of this patent is extended or adjusted under 35 U.S.C. 154(b) by 0 days.

(21) Appl. No.: 09/454,429

(22) Filed: Dec. 3, 1999

Related U.S. Application Data
(60) Provisional application No. 60/110,712, filed on Dec. 3, 1998.

(51) Int. Cl.[7] ................................................. G01R 1/40
(52) U.S. Cl. ....................... 204/600; 204/601; 204/603; 204/604; 204/452; 436/63; 356/344; 250/458.1
(58) Field of Search ................................. 204/600, 603, 204/601, 452, 604; 436/63; 356/344; 250/458.1

(56) References Cited

U.S. PATENT DOCUMENTS

| 5,061,361 | A | * | 10/1991 | Gordon ........................ 204/452 |
| 5,483,075 | A | * | 1/1996 | Smith et al. ................ 250/458.1 |
| 5,582,705 | A | * | 12/1996 | Yeung et al. ................. 204/603 |
| 5,584,982 | A | * | 12/1996 | Dovichi et al. .............. 204/603 |
| 5,597,468 | A | * | 1/1997 | Lauer et al. ................. 204/604 |
| 5,616,228 | A | * | 4/1997 | Nasu et al. .................. 204/603 |
| 5,903,348 | A | * | 5/1999 | Melman et al. ............. 356/344 |
| 6,156,177 | A | * | 12/2000 | Takahashi et al. ........... 204/452 |
| 6,156,576 | A | * | 12/2000 | Allbritton et al. ............. 436/63 |

* cited by examiner

Primary Examiner—Jill Warden
Assistant Examiner—Brian Sines
(74) Attorney, Agent, or Firm—F. Chau & Associates, LLP

(57) ABSTRACT

A multichannel electrophoretic cassette structure is disclosed comprising distinct regions for loading and detection with different spacing between channels. A method and an apparatus are further disclosed enabling multicolor fluorescent detection from a non-coplanar bundle of multiple channels. A method for fabricating monolithic multichannel cassettes for electrophoresis and fluorescent detection is also described.

9 Claims, 8 Drawing Sheets

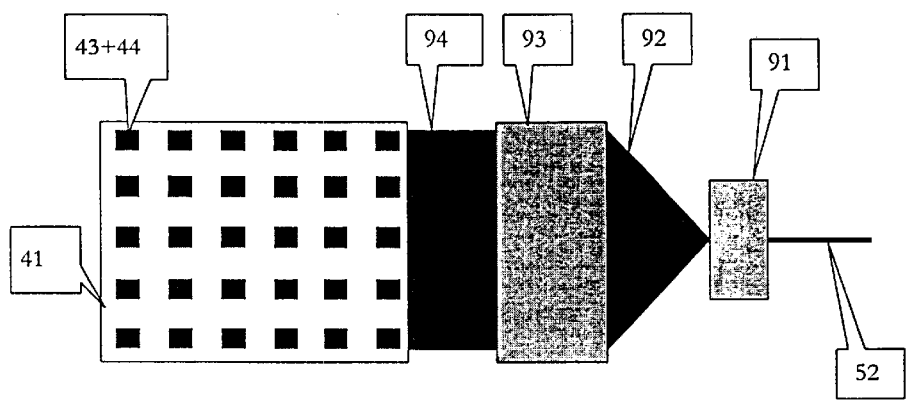
Figure 9
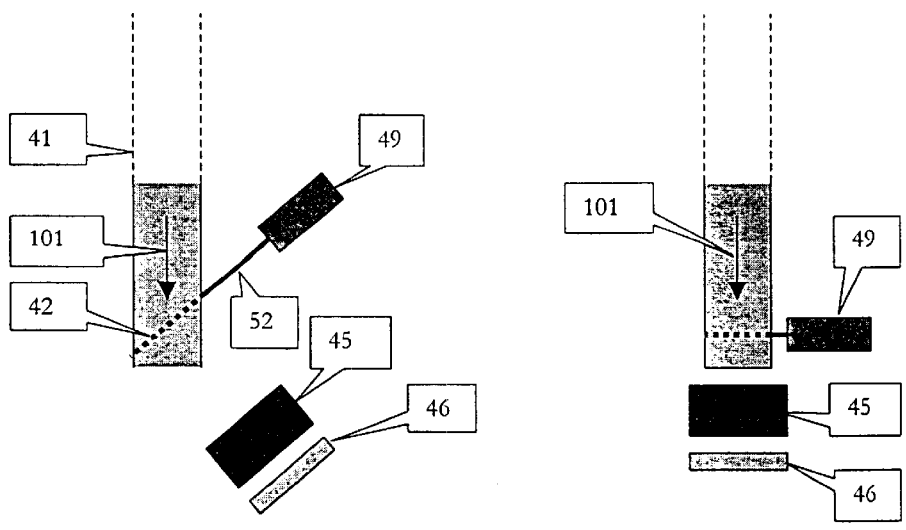
FIG 10a.   FIG. 10b.
Figure 10

MULTICAPILLARY BUNDLE FOR ELECTROPHORESIS AND DETECTION FOR DNA

CROSS-REFERENCE TO RELATED APPLICATIONS

This application claims priority to Provisional Application Serial No. 60/110,712 filed Dec. 3, 1998 and incorporated herein by reference.

GOVERNMENTAL INFORMATION

The U.S. Government has a license in this invention and the right in limited circumstances to require the patent owner to license others on reasonable terms of grant number HG01487 awarded by the National Institute of Health (NIH).

TECHNICAL FIELD

The present invention relates to a method and apparatus for DNA electrophoresis and detection.

BACKGROUND

Electrophoretic lanes are widely used for separating multi-component samples ranging from small inorganic ions to large biological molecules. DNA electrophoresis is commonly performed with polyacrylamide gel placed between two glass plates. In recent years, the method of capillary electrophoresis has been developed, which alleviates the dissipation of Joule heat and permits the application of higher voltage, thus speeding up the electrophoresis separation process. In capillary electrophoresis, a buffer-filled capillary is suspended between two reservoirs filled with a buffer liquid. An electric field is applied between the two ends of the capillary. The potential difference that generates the electric field is in the range of kilovolts. Multi-component samples are typically injected under the influence of an electrical field. The samples migrate under the influence of electric field, with components of the sample being electrophoretically separated. After the separation, the components are detected by a detector.

One of the important applications of electrophoretic separation is for DNA sequencing. The use of capillary electrophoresis has improved DNA sequencing rates. Part of the improvement in speed, however, was initially offset by the loss of the ability (inherent in slab gels) to accommodate multiple lanes in a single run. Highly multiplexed capillary electrophoresis, by making possible hundreds or even thousands of parallel sequencing runs, offers an attractive approach to overcoming the current throughput limitations of DNA sequencing instrumentation. Typically, an array of capillaries is held in a guide and the intake (cathode) ends of the capillaries are dipped into vials that contain samples. After the samples are taken in by the capillaries, the ends of the capillaries are removed from the sample vials and submerged in a buffer which can be in a common container or in separate vials.

The currently used multichannel electrophoretic arrays typically represent a coplanar arrangement of capillaries. This geometry has been chosen because of its convenience for detection, which is typically performed with the help of fluorescent tags (fluorophores) attached to the DNA fragments migrating along the electrophoretic lanes. The detection is typically effected by illuminating the lanes within a specially provided translucent portion near their anode end (the observation region) with a laser source that excites fluorescence. One of the common reasons for the conventional planar arrangement of the capillaries has been that it offers a straightforward way of positioning the photoreceiving matrix that detects the fluorescence from all lanes in parallel. Another common reason for the parallel arrangement of capillaries is due to the need for color resolution of different fluorescent markers, which is typically performed by spatially dispersing the emitted fluorescent radiation in the longitudinal (along the lanes) direction. The spatially dispersed radiation from all observation regions is then imaged onto a two-dimensional photoreceiving matrix, such as CCD or CMOS, using a high-aperture projection objective. Still another common reason for the parallel arrangement of capillaries is associated with the desire to illuminate all lanes at once with a laser beam, which propagates in the plane of the capillaries and at the same time transverse to their axes.

In recent years, several authors disclosed such multicapillary systems, see e.g., Quesada et al., "Multiple capillary DNA sequencer that uses fiber-optic illumination and detection", *Electrophoresis*, vol. 17, pp. 1841–1851 (1996). Moreover, multicapillary systems have been disclosed in which the capillaries themselves serve as light-guiding elements for the illumination beam, see, e.g., Yeung et al., "Multiplexed capillary electrophoresis system", U.S. Pat. No. 5,582,70 (1996) and Quesada et al., "Multi-capillary optical waveguides for DNA sequencing", *Electrophoresis*, vol. 19, pp. 1415–1427 (1998).

Therefore, a need exists for a non-planar arrangement of multiple capillary electrophoretic lanes which provide miniaturization of the electrophoretic carrier and which will significantly reduce the cost of multiple-lane DNA sequencing machines. A further need exists for a method for manufacturing monolithic cassettes, including multiple capillary lanes and a method and apparatus for parallel detection of fluorescent markers passing through the observation regions in a non-planar arrangement of multiple electrophoretic lanes.

SUMMARY

The present disclosure describes a non-planar arrangement of multiple capillary electrophoretic lanes, a technique for manufacturing monolithic cassettes, comprising such multiple capillary lanes and a method and apparatus for parallel detection of fluorescent markers passing through the observation regions in a non-planar arrangement of multiple electrophoretic lanes. The need for non-planar arrangement arises from the desire to miniaturize the electrophoretic carrier, which will significantly reduce the cost of multiple-lane DNA sequencing machines.

The present disclosure offers inventive solutions that circumvent all of the above-cited common reasons for choosing co-planar geometry of a multilane assembly. In the simplest embodiment, the photoreceiving matrix is arranged in a first plane inclined at an angle relative to the capillary axes, while the observation regions of different capillaries are arranged in a second plane which is also inclined at an angle relative to the capillary axes. For example, the first and second planes are parallel to each other inclined at 45 degrees relative to the capillary axes. The simultaneous illumination of multiple capillary lanes is effected by an array of modulated laser sources whose beams have a specially chosen spatial arrangement and direction relative to the capillary axes and to said first and second planes. Next, the need for spatial dispersion of fluorescent radiation into components corresponding to different fluorescent wavelengths is eliminated in accordance with the method for multicolor fluorescent detection recently disclosed by Gorfinkel et al., "Method and apparatus for identifying fluorophores", U.S. Pat. No. 5,784,157 (1998). Further, the need for waveguiding the incident radiation in the inventive method is substantially eliminated by using tightly packed capillaries of small cross-section. In a preferred embodiment, the capillaries have a rectangular or square cross-section of less than about 100 μm on the side. For example, a rectangular array of 96 such capillaries has an overall cross-section of less than 1 mm². As many as one thousand capillary lanes can be accommodated in a monolithic array of square cross-section about 3×3 mm. The present invention further discloses techniques for fabricating such multicapillary arrays. These techniques employ drawing a glass preform that has a pre-fabricated set of holes of desired shape (e.g., rectangular) and is similar to drawing hollow optical fibers or glass ferrules, see, e.g., MacChesney et al., "Materials development of optical fiber", *Journal of the American Ceramic Society*, vol. 73, pp. 3537–3556 (1990) and Anderson et al., "Optical fiber connector comprising a glass ferrule, and method of making same", U.S. Pat. No. 5,598,496 (1997). In one preferred embodiment, the preform is prepared with multiple holes to draw a monolithic multicapillary structure. In another preferred embodiment, a multicapillary bundle is fabricated by gluing or soldering together a multiplicity of single capillaries.

Still another aspect of the present invention pertains to loading tightly packed monolithic capillaries. In one of the preferred embodiments, this is provided by matching the capillary array cross-section with a similar array of charging pins on a silicon chip. In another preferred embodiment, the capillary assembly, which is monolithic in the observation region near the anode, is made loose like a brush near the cathode end. A special fixture holder is further provided that fixes the loose cathode ends of capillaries in a desired pattern. In a preferred embodiment, the loose cathode ends of the capillaries are arranged in a pattern that matches the common 96 well plate widely used in the preparation of biological samples.

DESCRIPTION OF THE DRAWINGS

FIG. 4*a*: side view; FIG. 4*b*: top view; FIG. 4*c*: fluorescent image projected onto a photoreceiving matrix;

FIG. 9 illustrates illumination of capillaries with the help of an optical line generator;

FIGS. 10*a–b* illustrate exemplary spatial arrangements of the capillaries, the optical source and the photoreceivers;

DETAILED DESCRIPTION OF PREFERRED EMBODIMENTS

The multicapillary bundle may be implemented either as a monolithic or quasi-monolithic structure or a loose assembly of individual capillaries. Monolithic structures may be obtained by drawing on a preform. Quasi-monolithic structures may also be obtained by a tight packing together of individual capillaries or smaller monolithic multicapillary units. We also envision intermediate structures, which may be monolithic or quasi-monolithic in one region and loose in another.

Figure 1:
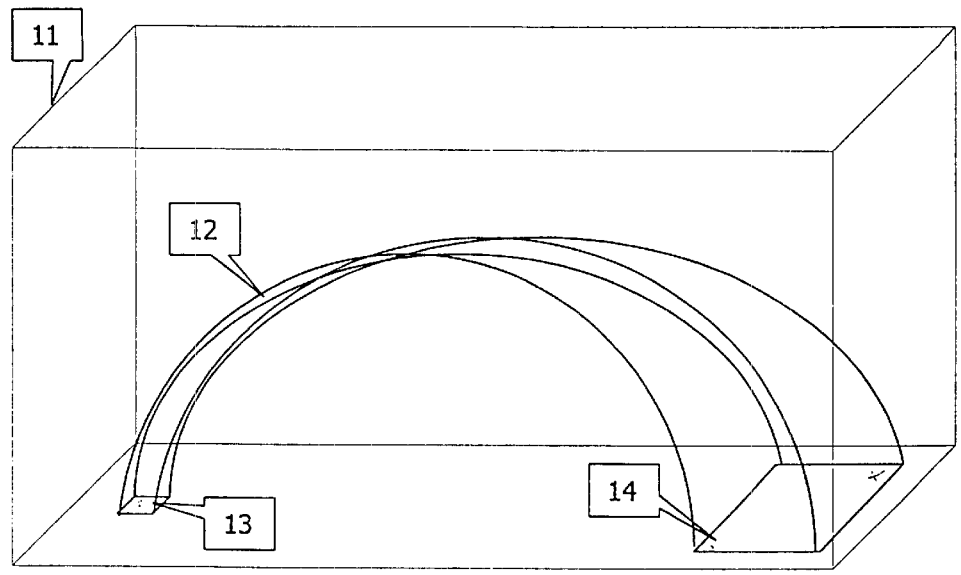
FIG. 1 illustrates the general structure of a multicapillary cassette.
Figure 2:
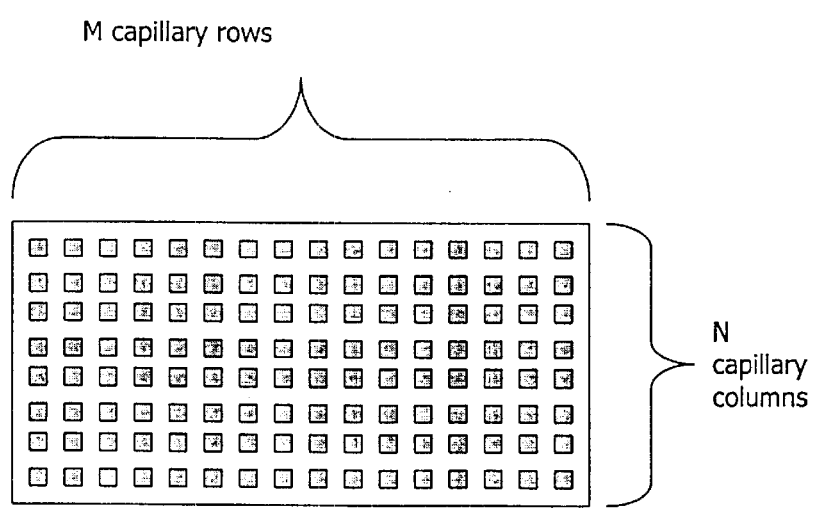
FIG. 2 illustrates the cross-section of the capillary assembly near the observation region.

Various versions of the multicapillary bundle can be characterized by the geometry of their cross-section at different positions along the capillary lanes, cf. FIG. 1. The geometry of the bundle is important in that it affect the way the operations of fluorescent detection and sample loading are performed. In every preferred embodiment, the cross-section of the multicapillary bundle in the region of detection is monolithic or quasi-monolithic and is characterized by a definite known pattern of capillaries of a desirable shape. For example said pattern may be periodic in two dimensions as illustrated in FIG. 2. The desirable shape of the cross-section of the individual capillary lanes in the detection region is determined primarily by the convenience of external illumination and collection of the fluorescent response. For example, said shape is rectangular or oval but it may also be hexagonal or some other polygonal shape. The shape of the bundle cross-section and that of individual capillaries need not be the same in other regions of the bundle as determined by the convenience of loading, efficiency of electrophoresis and facility of manufacturing.

In one preferred embodiment, the entire bundle is monolithic or quasi-monolithic. The loading end surface of the bundle may represent a flat surface perpendicular or inclined to the capillary axis. The surface may also be processed, e.g., mechanically or chemically, resulting in non-flat surface. In this embodiment the bundle cross-section may be constant or variable along the length of the bundle.

Figure 3:
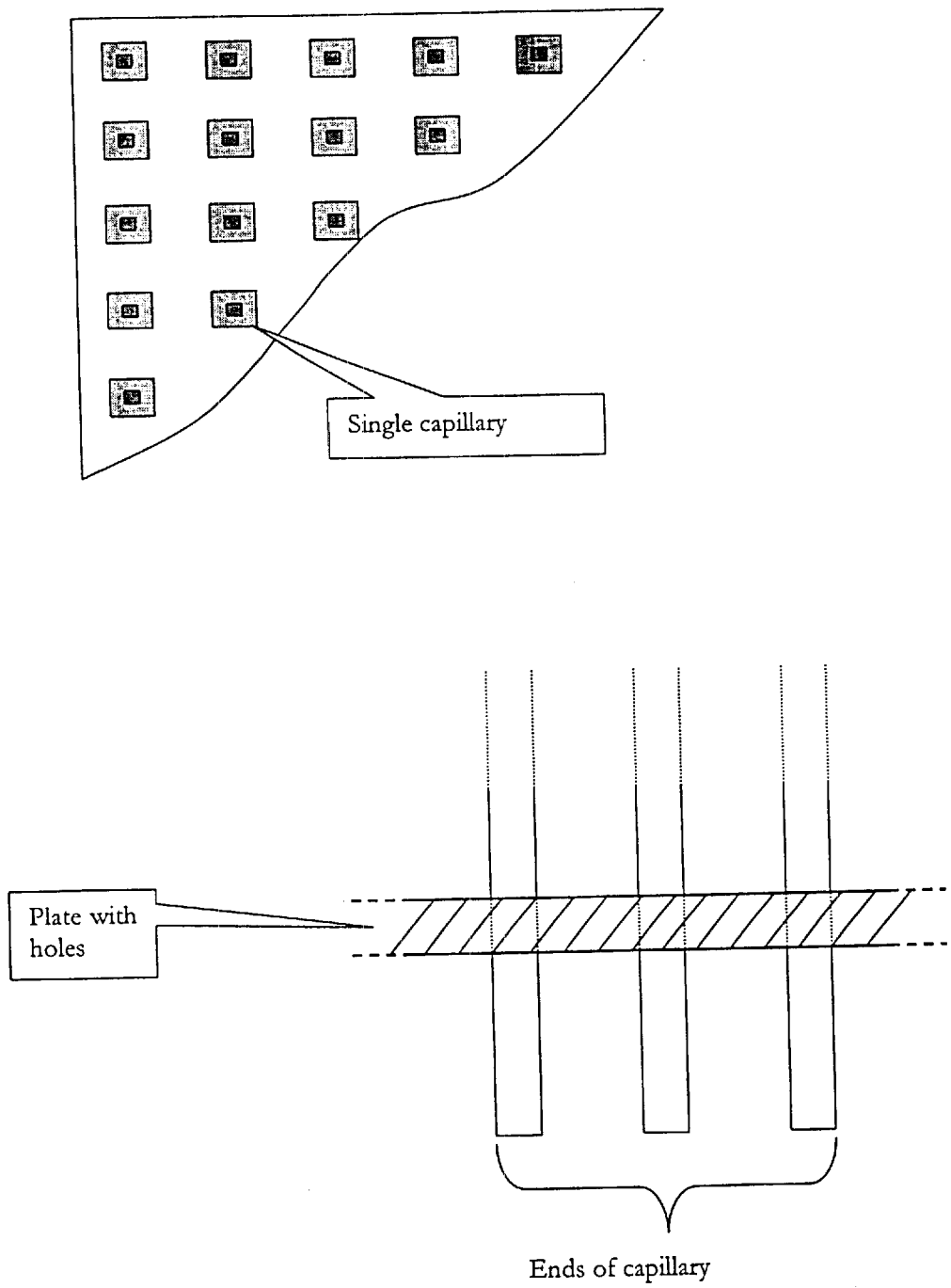
FIG. 3 illustrates the cross-section of the capillary assembly near the loading region.

In another preferred embodiment, the bundle is monolithic or quasi-monolithic in the detection region while loose in the loading region, as illustrated in FIG. 3. Loose capillary ends are fixed in a pattern determined by a specially provided fixture plate. In a preferred embodiment, this pattern matches the common 96-well plate containing DNA samples. Holes in the fixture plate are of desired shape, e.g., cylindrical, conical, or pyramidal, designed to tightly hold the capillaries. Fixation of the capillaries in the fixture plate can be done in a variety of ways, e.g., by gluing or soldering.

Loading Device

Loading of the DNA samples into the multicapillary bundle can be done by using a variety of known techniques employed for the injection of DNA samples into single capillary lanes. These techniques include, e.g., the mechanical transfer and electro-kinetic injection. The inventive techniques disclosed here relate to specific configurations that facilitate loading into a bundle of capillaries. Firstly, the loading device must be adapted to the cross-sectional dimensions of the bundle in the loading region. The preferred geometry of the loading device comprises one or more adapters that have a similar pattern as the bundle cross-section. Said adapters may be attached to the source of DNA samples, such as a multi-well plate or a micro-fluidic chip. Said adapters may also be attached to the capillary bundle in a removable or permanent fashion. The adapter may comprise a pattern of holes or protuberances that fit the capillary pattern. Connection between the adapter and the capillary pattern may be either male-to-female or female-to-male. Alternatively, the adapter may be elastic and have a flat surface with holes so that a tight connection is established simply by pressing the edge of the capillary bundle on the adapter.

The loading device may provide means for electrokinetic injection. To this end, it must be outfitted with one or more electrodes. The controlling voltage may be applied to different electrodes individually, so that different voltages are applied to different electrodes.

Referring to FIG. 1, spatial arrangement of elements of a preferred embodiment of the multicapillary cassette for DNA sequencing includes:

housing 11; multicapillary bundle 12; observation region 13; and loading region 14.

In FIG. 1, it is assumed that the anode and the cathode are placed outside the housing 11 so that capillaries continue beyond regions 13 and 14. The housing volume may be filled with a heat conducting fluid or other means for thermal control of the capillaries.

Referring to FIG. 2, a cross-section of the capillary assembly near the observation region is shown. The M×N array comprises rectangular capillaries arranged in M columns and N rows. The shape of capillaries can be rectangular, square, elliptic, or any other selected for the convenience of illumination and collection of fluorescence. The capillary assembly in this region is a tightly packed bundle. In a preferred embodiment the assembly is monolithic obtained by drawing a preform with multiple holes of desired shape. In another preferred embodiment the assembly is made up of single, for example, rectangular capillaries, soldered or glued together using solder or glue of properly matched refractive index.

Referring to FIG. 3, a cross-section of the capillary assembly near the loading region is shown. Loose capillary ends are fixed in a pattern determined by the fixture plate. In a preferred embodiment, this pattern matches the common 96-well plate containing DNA samples. Holes in the fixture plate are of desired shape, e.g., cylindrical, conical, or pyramidal, designed to tightly hold the capillaries. Fixation of the capillaries in the fixture plate can be done in a variety of ways, e.g., by gluing or soldering. A thermal process based on the thermal expansion and contraction of the holes can also be used. In another preferred embodiment the capillary ends are not loose but are monolithic, for example, obtained by drawing on a preform. In such embodiments it is contemplated that the well plate from which samples are injected into capillaries is implemented as a microchip or a micro-assembly to match the miniature cross-section pattern of a monolithic multicapillary structure.

The arrangement of capillaries in a cross-section of the capillary assembly near the loading region may be organized in a different way from that near the observation region. While the total number of capillaries is obviously the same in both cross-sections their row x column pattern may be quite different. For example, one may still have a matrix of dimensions P×Q=M×N, where M and N refer to FIG. 2, but the factors P,Q are different from M,N.

To facilitate precise manipulation of the capillary bundle and its alignment relative to the loading device, special set of alignment marks may be provided, that is clearly visible or detectable in a cross-section of the bundle in the loading region. These marks may employ an optical or some other physical effect. In one preferred embodiment, the desired set of alignment marks is obtained by filling a reserved group of capillaries in the bundle with some easily detectable material. For example, said group of capillaries may be filled with some conducting or magnetic fluid, or some distinguishable optically contrast fluid, such as containing color luminescent or fluorescent species.

Figure 4A:
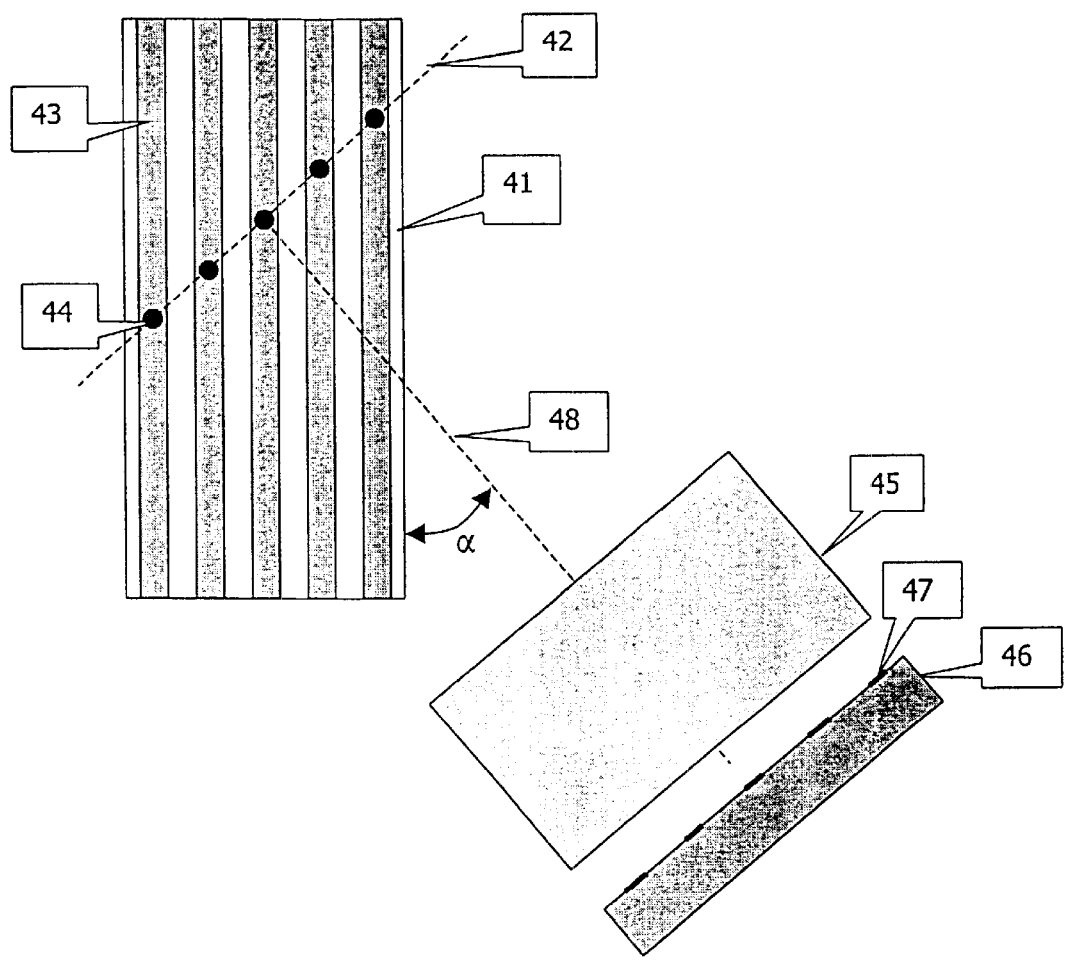
FIGS. 4*a–c* illustrate the spatial configuration of the capillary assembly, the illuminator and the photoreceiver in the observation region.
Figure 4B:
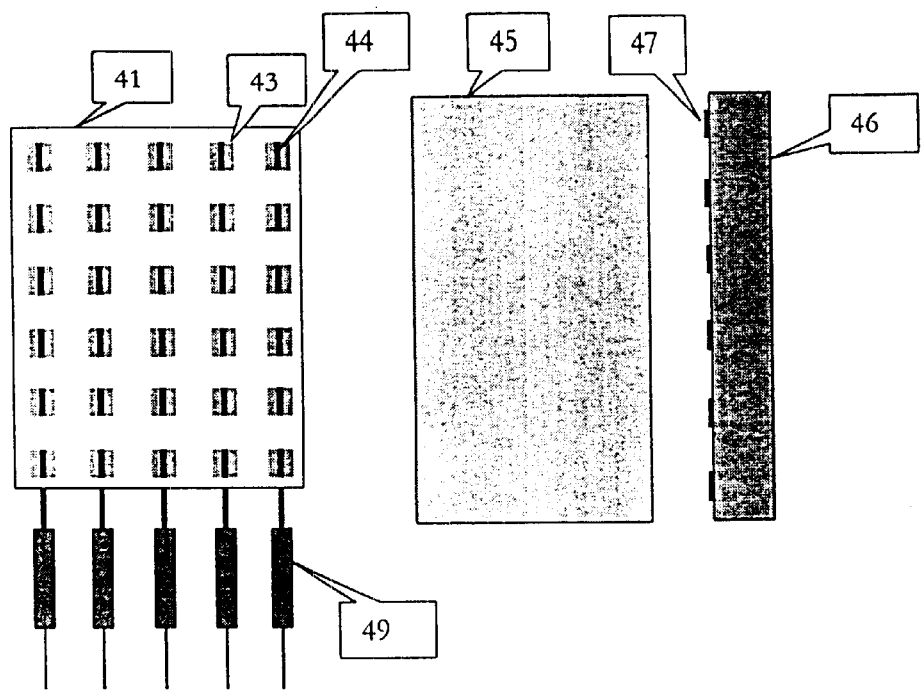
Figure 4C:
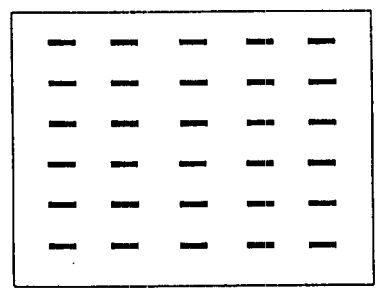

Referring to FIGS. 4*a–c*, an illustration of the spatial configuration of the capillary assembly, the illuminator and the photoreceiver in the observation region, is shown. FIG. 4*a* shows a side view of the relevant portion of the apparatus. FIG. 4*b* shows a top view of the relevant portion of the apparatus. FIG. 4*c* shows a planar view of the fluorescent image projected onto the target screen of the photoreceiving system. FIGS. 4*a–c* include: assembly (bundle) of capillaries 41; focal plane of the optical receiving system 42; one of the capillaries of the assembly 43; fluorescent zone 44 in one of the capillaries 43 of the assembly; optical receiving system 45, such as projection optics; photoreceiving system 46, such as CCD or CMOS, or PMT matrix; image of the fluorescent zones 47 on the target screen of the photoreceiving system 46; optical axis 48 of the optical receiving system with the angle between said optical axis and the capillary axes denoted by $\alpha$, for example, $\alpha=45°$; one of the optical paths 49, including projection optics, carrying the excitation beam from illumination sources.

The illumination sources are arranged so that the optical excitation beams they emit propagate in the focal plane 42 of the optical receiving system 45. Said excitation beams need not be parallel to each other but may be parallel. In a preferred embodiment, illustrated in FIG. 4*a*, the optical excitation beams propagate perpendicular to a plane containing a row of capillaries, i.e., perpendicular to the cross-section of the assembly displayed in the plane of FIG. 4*a*. In FIG. 4*b* the direction of illumination beams lies in the plane of the drawing and in the direction of sources 49. The image 47 on the target of the photoreceiver 46 is shown in FIG. 4*c* as a plane view.

To facilitate the spatial alignment of the capillary assembly, the illuminator and the photoreceiver in the observation region, the capillary bundle may be outfitted with alignment marks clearly visible or detectable in a cross-section of the bundle in the observation region, such as plane 42. For example, said set of markers may be obtained by reserving several capillaries in the bundle to be filled with some distinguishable fluorescent fluid or fluids.

Figure 5:
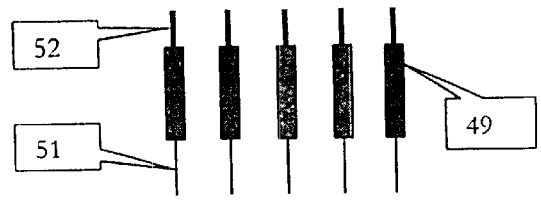
FIG. 5 illustrates a preferred structure of the illumination source.

Referring to FIG. 5, an illustration of the spatial arrangement of elements of the illumination system are shown and may include: an optical channel 51 delivering the desired combination of modulated spectral components from the optical source and a narrow excitation beam 52 directed onto the capillary assembly.

FIG. 5 displays separately a portion of FIG. 4*c* to illustrate the possibility of implementing the illumination system as a group of independent, not necessarily parallel, optical systems, each comprising a modulated source. In another preferred embodiment, illustrated in FIG. 7, the illumination is obtained from a single multiplexed optical source. In general, the number of independent optical sources can be smaller than, equal to or large than the number of illumination channels 52.

Figure 6:
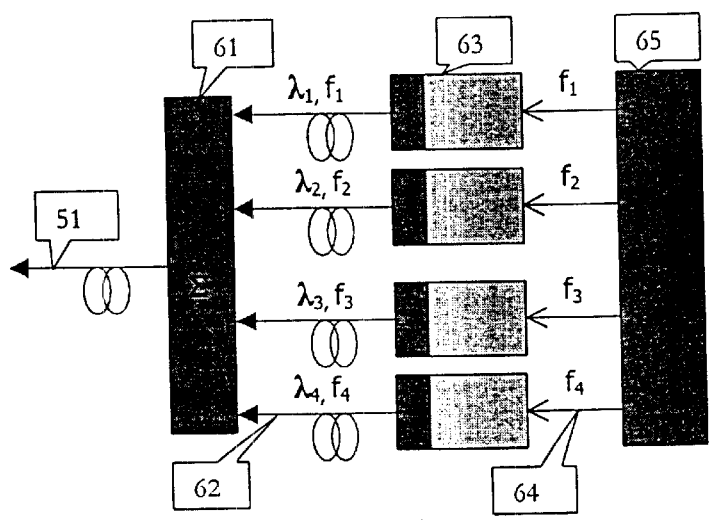
FIG. 6 illustrates an array of independently modulated optical sources and coupling of their radiation outputs into a single optical fiber.

Referring to FIG. 6, an illustration of an array of independently modulated optical sources coupled into a single optical path, for example, an optical fiber and may include: an optical coupler 61; optical channels 62, e.g., fibers, delivering modulated narrow-band optical spectral component to coupler 61; modulated narrow-band light source 63, e.g., diode laser, LED, or a gas or solid-state laser with an external modulator; electrical signals 64 modulating light sources 63, for example, at distinct radio frequencies $f_i$; the source of modulating signals 65, e.g., a modulated current driver for laser diode.

The narrow-band optical spectral components ($\lambda_1, \ldots, \lambda_4$) independently modulated at distinguishable radio frequencies ($f_1, \ldots, f_4$) are delivered to the inputs of the optical coupler 61 which combines these components into a single optical path 51, for example an optical fiber.

Figure 7:
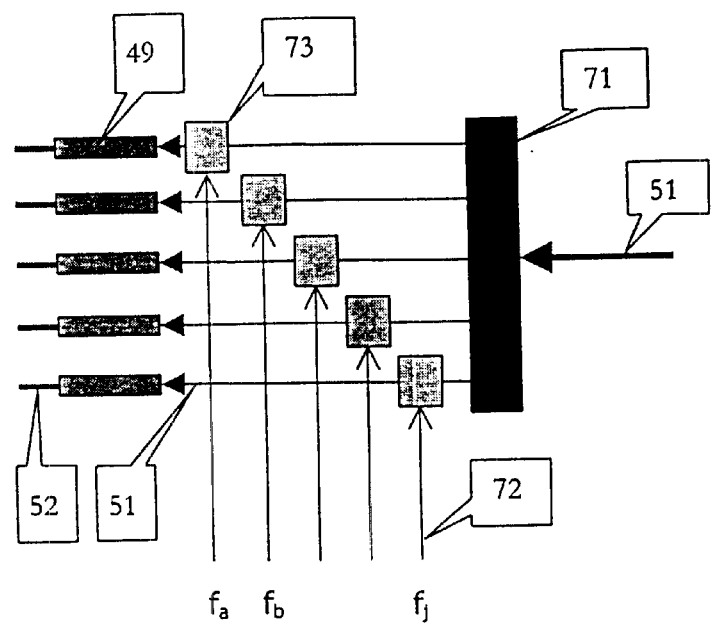
FIG. 7 illustrates the structure of a fiber-optic illumination system to provide independently modulated and reconfigurable optical beams.

Referring to FIG. 7, an illustration of a fiber-optical illumination system delivering a multiple independently modulated and reconfigurable optical beams may include: an optical demultiplexer or beam splitter 71; modulating electrical signals 72 at distinct radio frequencies; optical modulators 73, e.g., choppers, controlled by signal 72. Optical beam 51 containing multiple spectral components coupled into a single optical path is delivered to the input of a beam splitter 71 which provides at its multiple outputs a number of optical beams. These beams may or may not be similar in intensity or polarization. Each beam is modulated independently by modulators 73 controlled by electrical signals 72.

Figure 8:
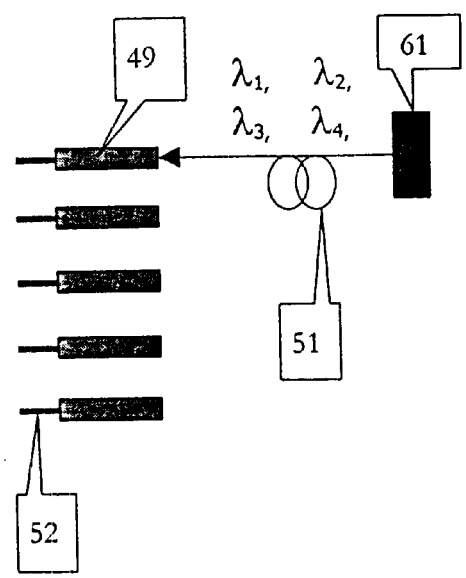
FIG. 8 illustrates the structure of a fiber-optic illumination system with a multiple independent light sources.

Referring to FIG. 8, an illustration of a fiber-optic illumination system with a multiple independent light sources is shown. Each of the narrow optical excitation beams 52 directed onto the capillary assembly comprise multiple modulated optical spectral components taken from the optical channel 51 which delivers the desired combination of modulated spectral components from the optical coupler 61. As illustrate in FIG. 6, said optical coupler 61 gathers multiple spectral components from a set of modulated light sources 63 and couples them into a single optical channel 1, for example an optical fiber.

Referring to FIG. 9, an illustration of capillary bundle illumination with the help of an optical line generator is shown which includes: an optical line generator 91; a divergent asymmetric beam of light 92; an asymmetric beam collimator 93; and a collimated laterally extended optical illumination beam 94. Optical line generator is inserted in the beam path before the capillary assembly. The narrow optical excitation beam 52 is transformed by the optical line generator 91 into a divergent asymmetric beam 92. The asymmetry of the beam means that the beam cross-section is highly asymmetric, e.g. elliptic rather than circular. In the plane where the divergent beam reaches collimator 93, said beam is extended in one direction so as to illuminate the full section of the multi-capillary assembly. In the other direction the beam remains as narrow as possible, preferably close to the original width of beam 52. The purpose of the collimator 93 is to transform the divergent beam 92 into a parallel (collimated) beam 94.

Another preferred embodiment of an optical line generator is to provides means for scanning the beam 52 laterally over the full section of the multi-capillary assembly. In contrast to the conventional beam scanners which scan by changing the angular direction of a pencil beam, the scanned beam according to present invention is obtained by parallel transfer of a pencil beam, retaining the same angular orientation. Such scanning means are well known to those skilled in the art.

Referring to FIGS. 10a–b, an illustration of exemplary spatial arrangements of the capillary bundle relative to the optical source and the photoreceiver are shown and include:
a direction along an electrophoretic lane 101 indicating the average motion of labeled DNA fragments. FIG. 10a shows an arrangement similar to FIG. 4a except that the narrow optical excitation beam 52 is incident on the capillary assembly 41 at an oblique angle. The beam 52 and optical paths 49 represent a whole plane of beams 52 and paths 49 which in the drawing 10a is perpendicular to the plane of the drawing. Similar representation is assumed in FIG. 10b which shows the same elements as FIG. 10a but arranged at still another relative orientation. In FIG. 10b the plane of beams 52 and paths 49 is perpendicular to capillary axes (direction 101). The projection optics 4 is oriented so that the photoreceiving system 46 receives the image of a plane perpendicular to direction 101.

Figure 11:
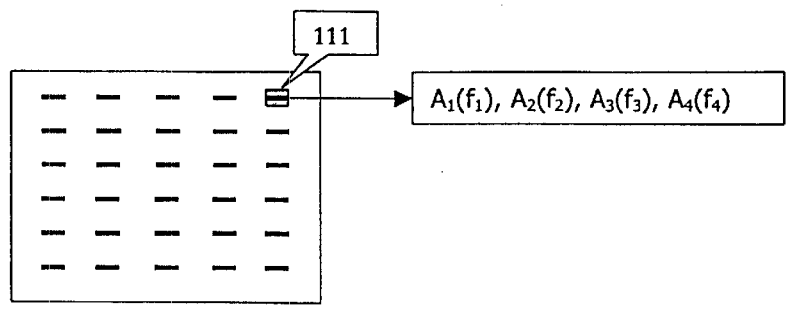
FIG. 11 illustrates the reception of fluorescent signal by a two-dimensional photoreceiving matrix.

Referring to FIG. 11, reception of the fluorescent signal by a two-dimensional photoreceiving matrix is shown and includes: one pixel of a two-dimensional photoreceiving matrix 111. The electric output of each pixel represents a set of amplitudes $A_j(f_j)$ of received optical signal at radio frequencies of modulation.

Figure 12:
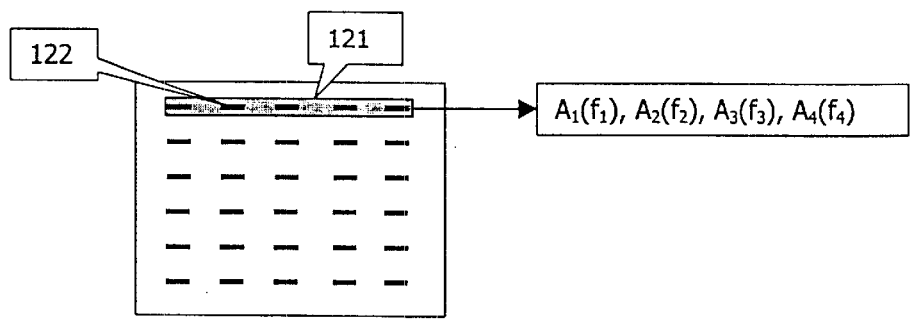
FIG. 12 illustrates the reception of fluorescent signal by a linear photoreceiving array.

Referring to FIG. 12, reception of the fluorescent signal by a linear photoreceiving array includes one pixel of the linear photoreceiving array 121 and a projection of a single fluorescent spot 122 from a single capillary element of one the N capillary columns (see FIG. 2).

Figure 13:
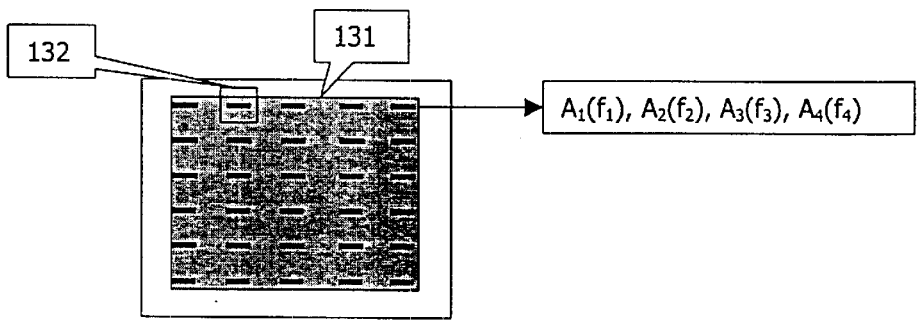
FIG. 13 illustrates the reception of fluorescent signal by a wide area photoreceiver.

Referring to FIG. 13, reception of fluorescent signals by a wide area photoreceiver includes a target 131 of wide area photoreceiver and a projection 132 of a single fluorescent spot from a single capillary element of the M×N capillary bundle (FIG. 2).

Commonly assigned provisional applications U.S. application Ser. No. 60/110,714 and 60/110,720 are incorporated herein by reference.

Having described preferred embodiments of a system and method of the invention (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A multichannel electropheretic cassette structure comprising:

a housing;

a plurality of capillaries arranged in a non-planar bundle;

a loading region for loading biological molecules into the capillaries;

an observation region for observing biological molecules in said plurality of. capillaries;

said plurality of capillaries extending in an arc between said loading region and said observation region;

a photodetector arranged in a first plane inclined at an angle relative to an axis of the plurality of capillaries at said observation region;

said photodetector simultaneously imaging each capillary in the non-planar bundle, enabling multicolor fluorescent detection of biological molecules in said plurality of capillaries.

2. The multichannel electrophoretic cassette structure of claim 1, further comprising known capillary patterns for give cross-sections of the arc.

3. The multichannel electrophoretic cassette structure of claim 1, wherein the loading region comprises a first cross-sectional dimensionality and the observation region comprises a second cross-sectional dimensionality.

4. The multichannel electrophoretic cassette structure of claim 3, wherein the capillaries have a known variable cross-section organization between the loading region and the observation region.

5. The multichannel electrophoretic cassette structure of claim 1, wherein the housing includes a heat conducting fluid.

6. The multichannel electrophoretic cassette structure of claim 1, wherein the housing includes a means for thermal control of the capillaries.

7. The multichannel electrophoretic cassette structure of claim 1, further comprising an alignment marker detectable in a cross-section of the capillary bundle.

8. The multichannel electrophoretic cassette structure of claim 7, wherein the alignment marker is a fluid in a predetermined capillary of the capillary bundle.

9. The multichannel electrophoretic cassette structure of claim 1, further comprising an illuminator proximate to the observation region at an angle to the photodetector.

* * * * *

UNITED STATES PATENT AND TRADEMARK OFFICE
CERTIFICATE OF CORRECTION

PATENT NO.   : 6,464,852 B1
DATED        : October 15, 2002
INVENTOR(S)  : Gorfinkel et al.

It is certified that error appears in the above-identified patent and that said Letters Patent is hereby corrected as shown below:

<u>Title page,</u>
Item [73], Assignee, replace "State University of the State of New York" with
-- Research Foundation of State University of New York --

Signed and Sealed this

Fourth Day of February, 2003

JAMES E. ROGAN
*Director of the United States Patent and Trademark Office*